United States Patent
Bisgaier et al.

(12)

(10) Patent No.: US 6,231,847 B1
(45) Date of Patent: May 15, 2001

(54) METHOD OF TREATING VASCULAR PROLIFERATIVE RESPONSES

(75) Inventors: Charles Larry Bisgaier, 3605 Tanglewood Dr., Ann Arbor, MI (US) 48105; Uday Saxena, 2900 Galahad Dr., Atlanta, GA (US) 30345

(73) Assignees: Charles Larry Bisgaier, Ann Arbor, MI (US); Uday Saxena, Atlanta, GA (US)

( * ) Notice: Subject to any disclaimer, the term of this patent is extended or adjusted under 35 U.S.C. 154(b) by 0 days.

(21) Appl. No.: 09/264,449

(22) Filed: Mar. 8, 1999

Related U.S. Application Data

(63) Continuation of application No. 08/909,419, filed on Aug. 11, 1997, now abandoned.

(51) Int. Cl.[7] .................................................. A61K 31/785
(52) U.S. Cl. ........................ 424/78.08; 424/929; 424/930
(58) Field of Search ................................. 424/78.08, 929, 424/930

(56) References Cited

U.S. PATENT DOCUMENTS 5,032,608 * 7/1991 Dudrick ............................... 574/396

OTHER PUBLICATIONS

B.J. Auerbach et al J. Biol. Chem. L.A.124: 142510 27 (3), 1329–35 1996.*

U. S Saxena et al (1995) 15 (8) 1240–7 Arterio. Thromb. Vasc. Biol.*

* cited by examiner

*Primary Examiner*—Peter F. Kulkosky
(74) *Attorney, Agent, or Firm*—Arnall Golden & Gregory, LLP

(57) ABSTRACT

This invention relates to a method of treating vascular proliferative responses in a patient that comprises intravenously administering to the patient a proliferative response inhibiting amount of poly(arginine).

10 Claims, No Drawings

METHOD OF TREATING VASCULAR PROLIFERATIVE RESPONSES

This application is a Continuation of Ser. No. 08/909,419 filed Aug. 11, 1997 now abandoned.

FIELD OF THE INVENTION

This invention relates to a method of treating vascular proliferative responses.

BACKGROUND OF THE INVENTION

Vascular proliferative disorders are conditions within the walls of blood vessels, including arteries and veins, which result in occlusion or blockage of blood flow. A common vascular proliferative disorder is restenosis. Restenosis is a major clinical problem associated with coronary angioplasty and other medical procedures. Restenosis generally occurs within about 0 to 6 months in about 30% to 50% of patients who undergo balloon angioplasty to clear clogged coronary arteries in an effort to prevent and treat heart disease due to occluded arteries. The resulting restenosis causes substantial patient morbidity and health care expenses.

The process of restenosis is initiated by injury of the vessel, with the subsequent release of thrombogenic, vasoactive, and mitogenic factors. Endothelial and deep-vessel injury leads to platelet aggregation, thrombus formation, inflammation, and activation of macrophages and smooth-muscle cells. These events induce the production and release of growth factors and cytokines, which in turn may promote their own synthesis and release from target cells Thus, a self-perpetuating process is initiated.

There currently are no effective treatments available for restenosis. Accordingly, a major medical need exists for effective treatments for restenosis and other vascular proliferative disorders. We have now discovered that poly(arginine) can be used to treat vascular proliferative disorders such as restenosis.

SUMMARY OF THE INVENTION

Provided by the present invention is a method of inhibiting a vascular proliferative response in a patient that comprises intravenously administering to the patient a proliferative response inhibiting amount of poly(arginine).

In one embodiment of the invention, the patient is a patient who is to undergo or who has undergone angioplasty.

In another embodiment of the invention the patient is a patient who is to undergo or who has undergone a graft.

In another embodiment of the invention, the patient is a patient who is to undergo or who has undergone a shunt.

In another embodiment of the invention, the patient is a patient who is to undergo or who has undergone a transplant.

In a preferred embodiment of the invention, the proliferative response is restenosis.

In one embodiment of the invention, the poly(arginine) is a homopolymer.

In another embodiment of the invention, the poly(arginine) is a copolymer.

In another embodiment of the invention, the poly(arginine) has a weight-average molecular weight in the range of about 5,000 to about 30,000.

DETAILED DESCRIPTION OF THE INVENTION

The present invention provides a method of treating a vascular proliferative response in a patient, the method comprising intravenously administering to the patient a proliferative response inhibiting amount of poly(arginine).

The term "treating" means to ameliorate the symptoms of a proliferative response. The term treating also includes the prophylactic inhibition of a proliferative response. Poly(arginine) can be administered to a patient who is undergoing a proliferative response, such as a patient who is suffering from restenosis. In addition, certain patients are at risk of undergoing a proliferative response. Those patients include, but are not limited to, patients who have undergone or who will undergo balloon angioplasty, or graft, shut or transplant procedures. In such cases, it is desirable to administer poly(arginine) as a prophylactic measure to help inhibit a proliferative response or to ameliorate the symptoms of a proliferative response that has commenced.

The term "patient" means all animals, including humans. The patients to be treated by the present method are patients who suffer from a proliferative response or who are at risk for having a proliferative response. Those skilled in the art are readily able to identify patients who suffer from a proliferative response. For example, restenosis results in a blockage of a blood vessel. Thus, the presence of restenosis may be determined by observing the blood flow in the blood vessels, which is a common practice that is well know to those skilled in the art. The patients at risk for having a proliferative response include patients who have undergone or who are to undergo a medical procedures such as angioplasty, grafts, shunts or transplants, among others.

The poly(arginine) is administered to the patient in a proliferative response inhibiting amount. The amount of poly(arginine) administered will vary with each patient to be treated, and the amount can depend on the weight of the patient, and the severity of the proliferative response, among other factors. The amount of poly(arginine) administered to a patient can readily be determined by one skilled in the art by simply administering a quantity of poly(arginine) and observing the results. For example, in a patient having restenosis, poly(arginine) is administered and the rate of blood vessel occlusion monitored by watching the blockage of blood flow in the vessel.

An example of a suitable dosage of poly(arginine) for a typical human patient is a dose the range of about 10 mg/day to about 10,000 mg/day. Preferably, the dosage is in the range of about 100 mg/day to about 2,000 mg/day.

The poly(arginine) is administered intravenously to the patient. The administration can be at once or over a period. If over a period, the poly(arginine) can be administered in several finite quantities or continuously. Preferably, the poly(arginine) is administered continuously over a period.

The term "poly(arginine)" means a polymer that contains the amino acid monomer arginine. The poly(arginine) can be a homopolymer made solely of arginine or a copolymer that contains arginine monomer units. The copolymer can be any type of copolymer including graft, block or random copolymers, among others. For example, the poly(arginine) copolymer may contain other amino acid monomers such as lysine or histidine. Similarly, the poly(arginine) copolymer may contain monomers such as vinyl acetate, which can be hydrolyzed to give vinyl alcohol. It is noted that any physiologically acceptable monomer may be part of the copolymer along with the monomer arginine. In a most preferred embodiment, the poly(arginine) is a homopolymer.

The weight-average molecular weight of the poly(arginine), whether copolymer or homopolymer, is typically in the range of about 2,000 to about 100,000. Preferably, the weight-average molecular weight of the poly(arginine) is in the range of about 5,000 to about 30,000. Most preferably the poly(arginine) has a weight-average molecular weight in the range of about 8,000 to about 12,000.

Poly(arginine) homopolymer can be easily prepared by methods well known to those skilled in the art or can be obtained from Sigma Chemical Company, St. Louis, Mo. Similarly, the synthesis of poly(arginine) copolymers are well known to those skilled in the art.

When the poly(arginine) is a copolymer, the amount of arginine found in the polymer is in the range of about 1% to about 99% by weight of the copolymer. Preferably, the arginine is found in the range of about 30% to about 99% by weight of the copolymer. Most preferably, the poly(arginine) is found in the range of about 50% to about 99% by weight of the copolymer.

The poly(arginine) is typically administered to the patient as part of a pharmaceutically acceptable solution. Compositions suitable for administration may comprise physiologically acceptable sterile aqueous or nonaqueous solutions. Examples of suitable aqueous and nonaqueous carriers, diluents, solvents or vehicles include water, saline, ethanol, polyols (propyleneglycol, polyethyleneglycol, glycerol, and the like), suitable mixtures thereof, vegetable oils (such as olive oil) and injectable organic esters such as ethyl oleate.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

In addition, the poly(arginine) can be a poly(arginine) salt. Examples of suitable salts include, but are not limited to, the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to ammonium, tetramethylammonium, tetraethylammonium, methylamine, dimethylamine, trimethylamine, triethylamine, ethylamine and the like. (See, for example, Berge S. M., et al., "Pharmaceutical Salts," *J. Pharm. Sci.*, 66:1–19 (1977) which is incorporated herein by reference.) Preferably, the poly (arginine) is a hydrochloride salt.

EXAMPLES

Lipoprotein accumulation in the subendothelium of blood vessels is an important step in the pathogenesis of restenosis. The in vivo study presented below shows that lipoprotein accumulation in blood vessels is inhibited by the administration of poly(arginine)

Materials and Methods

Mice

Apolipoprotein E (ApoE-/-) deficient mutant mice (C57BL/6J-Apoe$^{mlUnc}$) were obtained from The Jackson Laboratory, Bar Harbor, Me. Offspring of these animals were used for the studies.

Surgical Procedure

Mice were surgically fitted with subcutaneous Alzet mini-osmotic pumps (Alzet pump Model 2002, Alza Corporation, Palo Alto, Calif.) to continuously deliver an intravenous solution of saline or 50 mg/ml L-poly(arginine) having a weight-average molecular weight of about 10,800 (Sigma Chemical Company, St. Louis, Mo.) in saline through the jugular vein. Prior to surgery, mice were maintained on a chow diet, and were of similar age (114±5 days, saline pump recipients, 119±2 days, poly(arginine) pump recipients) on the day of surgery. Since the pumps used can only deliver substance over 14 days, a catheter was devised so that the subcutaneous pumps could be replaced twice (every 13–15 days) over the duration of the 41 to 42 day treatment period. Once the pumps were implanted, mice were allowed free access to a high fat high cholesterol (HFHC) diet, which contained 1.25% cholesterol, 16% fat (5% soy bean oil, 7.5% cocoa butter, and 3.5% coconut oil), and 0.5% cholic acid (Diet D12336; Research Diets, Inc., New Brunswick, N.J.). Under sterile conditions, the pumps were prefilled with 0.2 mL of L-poly(arginine) or saline the evening before the surgery. To implant the pumps, mice were shaved, and the skin washed. The mice were initially anaesthetized with isoflurane (Anaquest, Madison, Wis.) and maintained under anesthesia with isoflurane during the surgical procedure. An incision was made and the jugular vein exposed. A step-down catheter was built from polyethylene tubing to attach and therefore allow the pump contents to flow into the jugular vein. To replace pumps at 2-week intervals, mice were anesthetized, and as above, an incision was made and the spent pump was replaced with a fresh pre-filled pump.

Lipoprotein Analysis

Blood samples were obtained from the treated mice at the time of sacrifice. In addition, for comparative purposes of lipoprotein profiles, blood samples were taken from non-treated apoE deficient mice maintained on chow. Plasma total cholesterol was determined enzymatically. Cholesterol distribution among lipoproteins was determined on a Rainin HPLC (Rainin Instrument Company, Woburn, Mass.) by high performance gel chromatography on a Superose 6 column (Pharmacia LBK Biotechnology, Uppsala, Sweden) by on-line post column analysis. Rainin Dynamax software was used to collect and analyze data.

Tissue Fixation

After 6 weeks on the HFHC diet, the saline and the poly(arginine) treated mice were sacrificed by $CO_2$ inhalation, a cardiac blood sample was obtained, and the heart plus the proximal aorta were removed, the tissues formalin fixed, and embedded in a commercially available embedding medium for frozen tissue specimens, such as TISSUE TEK® OCT compound, which is available from Miles Laboratories, Inc., Diagnostics Division, Elkhart, Ind. After embedding, the tissues were sectioned through the aortic valve and stained with hematoxylin and eosin.

Results

Intravenous saline and poly(arginine) containing Alzet pumps were installed for a 41- to 42-day period in four (3 females and 1 male) and five (3 females and 2 males) apoE-/- mice, respectively. To ensure a continuous delivery of saline or poly(arginine), the pumps were replaced twice at 13 to 15 day intervals over. Mice were maintained on chow prior to surgery and of nearly identical age at surgery. Within one day after each surgical procedure, the mice were lively and consuming their diet.

At sacrifice, plasma total cholesterol and triglycides were similar in the saline-treated (Cholesterol, 1794±173;

Triglycerides, 302±21 mg/dL) compared to the poly (arginine)-treated (Cholesterol, 2590±564; Triglycerides, 366±79 mg/dL) apoE-/- mice. Lipoprotein total cholesterol profiles were similar in all animals fed the HFHC containing the pumps and significantly elevated when compared to pre-surgical apoE-/- mice maintained on chow.

Dissection of the mice revealed striking differences in the luminal appearance of the aorta. In the saline-treated mice, the aortas were white and opaque, indicating lipoprotein deposition, while aortas from the poly(arginine) treated mice were largely translucent containing few discernable white plagues. To assess the extent of lipoprotein deposition in these mice, we specifically sectioned the aortic valve region.

In this region, all mice had some degree of lipoprotein deposition; however, the disease extent was strikingly different between the saline-infused and the poly(arginine)-infused mice. Most remarkable was the extent of crystalline cholesterol deposits in the saline-treated mice, with markedly less accumulation in the poly(arginine)-treated mice. Although the poly(arginine)-infused mice contained crystalline clefts, their size did not approach those observed in the saline-infused mice.

What is claimed is:

1. A method of inhibiting a vascular proliferative response in injured vasculature resulting from a medical procedure, the method comprising intravenously administering to the patient a proliferative response inhibiting amount of poly (arginine) in a dosage range of from 10 mg/day to about 10,000 mg/day.

2. The method of claim 1 wherein the patient is a patient who is to undergo or who has undergone angioplasty.

3. The method of claim 1 wherein the patient is a patient who is to undergo or who has undergone a graft.

4. The method of claim 1 wherein the patient is a patient who is to undergo or who has undergone a shunt.

5. The method of claim 1 wherein the patient is a patient who is to undergo or who has undergone a transplant.

6. The method of claim 1 wherein the proliferative response is restenosis.

7. The method of claim 1 wherein the poly(arginine) is a homopolymer.

8. The method of claim 1 wherein the poly(arginine is a copolymer.

9. The method of claim 1 wherein the poly(arginine) has a weight-average molecular weight in the range of about 5,000 to about 30,000.

10. The method of claim 1 wherein the poly(arginine) is administered in a dosage of up to about 2,000 mg/day.

* * * * *